US012767917B2

(12) United States Patent
Huang et al.

(10) Patent No.: US 12,767,917 B2
(45) Date of Patent: Oct. 20, 2026

(54) MICROFLUIDIC ELECTROPORATION DEVICE

(71) Applicant: ORIENTAL SYSTEM TECHNOLOGY INC., Hsin-Chu (TW)

(72) Inventors: Wen-Chie Huang, Hualien County (TW); Chein-Hsun Wang, Hsin-Chu (TW); Y. H. Chen, Taipei City (TW); Chin-Hsiang Chang, New Taipei City (TW); Jenping Ku, Hsinchu County (TW); Yu-Chih Liang, Hsinchu City (TW)

(73) Assignee: ORIENTAL SYSTEM TECHNOLOGY INC., Hsin-Chu (TW)

(*) Notice: Subject to any disclaimer, the term of this patent is extended or adjusted under 35 U.S.C. 154(b) by 758 days.

(21) Appl. No.: 18/128,441

(22) Filed: Mar. 30, 2023

(65) Prior Publication Data

US 2024/0327774 A1 Oct. 3, 2024

(51) Int. Cl.

| | |
|---|---|
| ***B01L 3/00*** | (2006.01) |
| ***C12M 1/42*** | (2006.01) |
| ***C12M 3/06*** | (2006.01) |

(52) U.S. Cl.

CPC ....... *C12M 35/02* (2013.01); *B01L 3/502761* (2013.01); *C12M 23/16* (2013.01);

(Continued)

(58) Field of Classification Search

None

See application file for complete search history.

(56) References Cited

U.S. PATENT DOCUMENTS

2006/0281168 A1* 12/2006 Futami .................. C12M 35/02 435/450

2012/0325747 A1* 12/2012 Rietman ................ B01D 65/00 210/651

(Continued)

OTHER PUBLICATIONS

International Food Information Service, Dictionary of Food Science and Technology, 2009, International Food Information Service (IFIS Publishing), 2nd Edition, p. 149 (Year: 2009).*

(Continued)

*Primary Examiner* — William H. Beisner
*Assistant Examiner* — Adrian Carreon
(74) *Attorney, Agent, or Firm* — HDLS IPR SERVICES; Chun-Ming Shih

(57) ABSTRACT

A microfluidic electroporation device for exogenous molecules transfection is disclosed. The microfluidic electroporation device includes an electroporation chamber assembly, an ultrasound vibrator, and a controller. The electroporation chamber assembly includes an input chamber for exogenous molecules, a MEMS filter, an activation chamber and a MEMS plate. The MEMS plate holds cells within individual cavity for electroporation. Both the MEMS filter and the MEMS plate are made of semiconductor process by wet etching and/or ICP dry etching with V-shaped cavities. The top surfaces of the MEMS filter and the MEMS plate are coated with metal layer for applying electric field during the electroporation process. The electroporation chamber assembly is attached to an ultrasound vibrator which is operated intermittently to allow cells to be fixed in the cavity of the MEMS plate during electroporation process and popped out for collection after electroporation process.

13 Claims, 5 Drawing Sheets

(52) U.S. Cl.
CPC .................. *B01L 2200/0663* (2013.01); *B01L 2300/0681* (2013.01); *B01L 2400/0439* (2013.01); *B01L 2400/06* (2013.01)

(56) References Cited

U.S. PATENT DOCUMENTS

| | | | | |
|---|---|---|---|---|
| 2013/0071304 | A1 * | 3/2013 | Jeon | B01L 3/502753<br>422/502 |
| 2019/0010516 | A1 * | 1/2019 | Tandon | C12M 35/02 |
| 2019/0100774 | A1 * | 4/2019 | Bernate | C12M 23/44 |
| 2019/0119624 | A1 * | 4/2019 | Tandon | C12M 23/16 |
| 2019/0292510 | A1 * | 9/2019 | Tandon | C12N 15/87 |
| 2020/0340014 | A1 * | 10/2020 | Chang | C12N 15/87 |
| 2022/0104544 | A1 * | 4/2022 | Jackson | A24F 40/05 |
| 2023/0173255 | A1 * | 6/2023 | Brooks | C12M 35/02<br>435/285.2 |
| 2023/0416080 | A1 * | 12/2023 | Sarajlic | G01Q 70/16 |

OTHER PUBLICATIONS

Yu-Cheng Lin, Electroporation microchips for gene transfection, 2005, Emerging Information Technology 2005 Conference (Year: 2005).*

* cited by examiner

MICROFLUIDIC ELECTROPORATION DEVICE

BACKGROUND

Technical Field

The present disclosure relates to a microfluidic electroporation device for transfection of the cells, which is based on an ultrasound vibration and a micro cavity catcher made by a MEMS (micro-electromechanical system) process.

Description of Related Art

Electroporation (EP) is the process of applying an electrical field across a cell membrane to temporarily form "pore" to enable the uptake of the exogenous molecules into the cytoplasm or the nucleus, thereby transfecting or transforming the cell.

In the past, a high voltage (for example, greater than 1000 V, or an electric field in the order of about kV/cm) needs to be applied to create temporary pore on a cell membrane, that may impact the viability of the cells to be transfected. By using microchannel method, the applied voltage may be reduced while maintaining the electric field strength for EP. An order of tens volts is capable to perform EP for microchannel method.

Hence, there is a need for a high speed, high efficiency and high viability device for transfection of cells.

In view of this, the inventors have devoted themselves to the aforementioned related art, researched intensively try to solve the aforementioned problems.

SUMMARY

Comparing to conventional bulk electroporation (EP), the spatial confinement method in micro scale provides numerous benefits such as rapid cargo uptake, precision dosage control and minimum cell disturbance.

Spatial confinement of electroporation methods includes microchannel (microfluidic) electroporation and microcapillary electroporation. The bench marks for electroporation are viability and efficiency, for example, the viability of transfected cells and how much percentage of cells or how many cells are transfected simultaneously.

For the spatial confinement of cells to be transfected, a microfluidic electroporation device having the micro cavities formed by MEMS (micro electrochemical system) process to be incorporated with the ultrasound vibrator is disclosed, that may be used to capture the cells within the cavities for electroporation process.

One objective of the present disclosure is to provide a microfluidic electroporation device for transfection, which has the features of high viability and high efficiency.

One embodiment of the present disclosure of the microfluidic electroporation device having a first stage filter, an electroporation chamber assembly, an ultrasound vibrator and a controller. The electroporation chamber assembly includes an input chamber with an inlet valve and an outlet valve, a MEMS filter, an activation chamber with an inlet valve and an outlet valve, and a MEMS plate attached to the activation chamber. The controller supplies driving power to the ultrasound vibrator with the capability of controlling amplitude, duty cycle and duration control. The controller also supplies electric driving voltage to the MEMS filter and the MEMS plate with the capability of controlling amplitude, pulse period and pulse number during electroporation process.

One embodiment of the MEMS filter to be used in the microfluidic electroporation device is with a funnel structure, and the MEMS filter is made of a silicon wafer with wet etching process and/or ICP (Inductively coupled plasma) etching process. The output hole of the funnel structure is more precisely controlled by the ICP etching process.

One embodiment of the MEMS filter has an output hole of the funnel structure being smaller than an input hole of the funnel structure. A diameter of the output hole is greater than or equal to 0.2 μm and less than or equal to 1 μm.

The top surface of the MEMS filter is coated with a metal layer connected to a negative terminal of the controller during electroporation process.

One embodiment of the MEMS plate has multiple V-shaped cavities, and has a metal layer connected to a positive terminal of the controller during electroporation process.

In some embodiments, the ultrasound vibrator is made of a piezoelectric device, such as polyvinylidene fluoride (PVDF), or lead zirconate titanate (PZT), etc. The ultrasound frequency of the ultrasound vibrator is between 20-200 Khz, and desirably is 40 khz.

In summary, the present disclosure discloses a microfluidic electroporation device for transfecting the exogenous molecules into the cells with high speed, high viability and high efficiency. The cells to be transfected are fixed in the cavities of the MEMS plate, and a low voltage pulse is applied during electroporation process to increase the viability. By using V-shaped cavity to capture the cells and applying positive voltage to the cell membrane, the present disclosure increases the viability of the cells. Further, the transfected cells may be collected by the ultrasound vibration with an external solution to be pushed out through the outlet valve connected with the activation chamber.

Therefore, comparing with the related art of micro-channel electroporation, the present disclosure is high speed and can be used in mass transfection of cells with the help of ultrasound vibrator and V-groove cavities to fix the cells.

BRIEF DESCRIPTION OF THE DRAWINGS

In order to further understand the techniques, means, and effects of the present disclosure for achieving the intended object. Please refer to the following detailed description and drawings of the present disclosure. The drawings are provided for reference and description only, and are not intended to limit the present disclosure.

DETAILED DESCRIPTION

The following are specific examples to illustrate some implementations of the present disclosure. A person skilled in the art may understand the advantages and effects of the present disclosure from the content disclosed in this specification. The present disclosure may be implemented or applied through other different specific embodiments, and various details in this specification may also be based on different viewpoints and applications, and various modifications and changes may be made without departing from the concept of the present disclosure.

The technical content and detailed description of the present disclosure are described below with the drawings.

Figure 1:
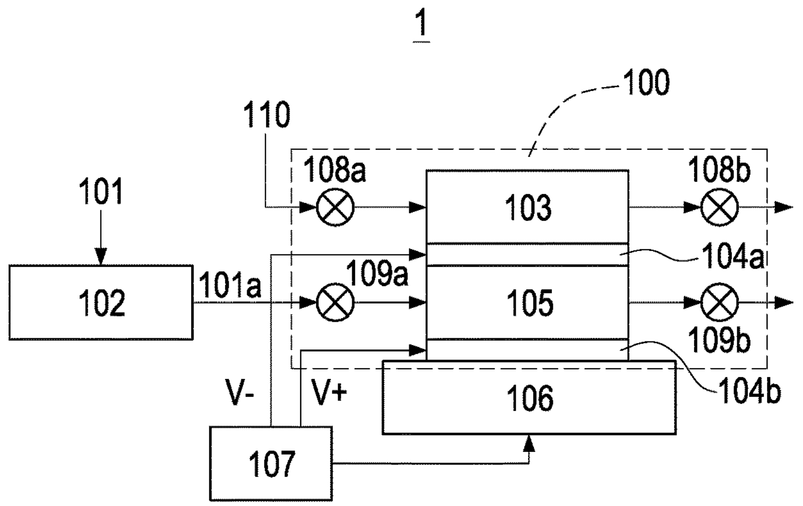
FIG. 1 is a block diagram of an embodiment of a microfluidic electroporation device of the present disclosure.

FIG. 1 is a block diagram of an embodiment of a microfluidic electroporation device 1 of the present disclosure. As shown in FIG. 1, the microfluidic electroporation device 1 includes a first stage filter 102, an electroporation chamber assembly 100, an ultrasound vibrator 106, and a controller 107.

The mixture solution 101 of the cells to be transfected is inputted to the microfluidic electroporation device 1. The first stage filter 102 may use conventional polymer membrane to filter out impurities or big particles, and only the cells 101*a* may pass through the first stage filter 102. The electroporation chamber assembly 100 includes an inlet valve 108*a*, an input chamber 103, an output valve 108*b*, a MEMS filter (top MEMS filter) 104*a*, an inlet valve 109*a*, an activation chamber 105, an output valve 109*b*, and a MEMS plate (bottom MEMS plate) 104*b*. The MEMS plate 104*b* has multiple cavities for holding the cells during electroporation process.

The input valve (control valve) 109*a* allows the cells 101*a* to enter the activation chamber 105 from the first stage filter 102. The exogenous molecules (for example, clonal DNA) 110 may pass through the input valve (control valve) 108*a* to enter the input chamber 103 and then pass through the MEMS filter 104*a* to enter into the activation chamber 105.

The MEMS filter 104*a* has a funnel structure (that is, a funnel shape type filter), and an output hole of the funnel structure is smaller than an input hole of the funnel structure. A diameter of the output hole is greater than or equal to 0.2 μm and less than or equal to 1 μm. The MEMS filter 104*a* may have a metal layer disposed on the top surface thereof. The metal layer is connected to a negative terminal V− of the controller 107 to receive a negative potential during electroporation process.

The MEMS plate 104*b* is attached to and located under the activation chamber 105. The MEMS plate 104*b* has multiple V-shaped cavities for holding the cells 101*a* in place during electroporation process. The V-shaped cavities of the MEMS plate 104*b* are formed by MEMS process, and each cavity is capable of holding one cell to be electroporated.

The electroporation chamber assembly 100 is disposed on the ultrasound vibrator 106. The ultrasound vibrator 106 allows the cells 101*a* to be dropped into cavity by intermittent vibration. During ultrasound vibration period, the cells 101*a* are jumping around and may fall into the cavity of the MEMS plate 104*b*. The ultrasound vibration amplitude, frequency, duty cycle and duration are controlled by the controller 107, such that majority of the cells 101*a* may be captured by each one of the cavities. The amplitude of ultrasound vibration may be decreased gradually after a predetermined time. The ultrasound vibration process is also called the cell-capture phase. After that, the electroporation phase (electroporation process) is described as below.

When the cell is located in the cavity, the exogenous molecules 110 pass through the inlet valve 108*a* to enter the input chamber 103. Each output hole of the MEMS filter 104*a* is mapped to be matched with each cavity of the MEMS plate 104*b*. By using gravity, the exogenous molecules 110 drop through the output hole of the MEMS filter 104*a* and are accelerated by electrical field to hit the target cell in the cavities of the MEMS plate 104*b* during electroporation process.

The ultrasound vibrator 106 is made of a piezoelectric device that converts electric drive to mechanical motion. The piezoelectric material such as polyvinylidene fluoride (PVDF) or lead zirconate titanate (PZT), etc., may be used for the ultrasound vibrator 106. In some embodiments, PZT is desirable material, which may be operated at a frequency range of 20 Khz-200 Khz, and desirably is 40 khz. The controller 107 may generate high frequency pulse trains and control the duty cycle, duration or amplitude of the ultrasound vibrator 106. By using ultrasound vibration, turbulence to the fluid may be created, such that the cells 101*a* may jump around and fall into the cavities of the MEMS plate 104*b*, when the ultrasound vibration 106 is terminated. One cell may be fixed in one cavity for cell mapping.

The MEMS plate 104*b* has a metal layer coated on the top surface thereof. The metal layer is connected to a positive terminal V+ of the controller 107 during electroporation process. Since the cell is located in the cavity, the membrane of the cell is tied to the positive potential during electroporation process. If the height of the activation chamber 105 is about 100 μm, a voltage of 10V is capable of creating an electrical field strength of 1000 V/cm, and that is sufficient for electroporation process with high viability of the cells 101*a*. During electroporation process, a DC (direct current) voltage with the order of tens volts is applied to the electrical connection terminal (the metal layers) of the MEMS filter 104*a* and the MEMS plate 104*b*. The controller 107 may control the voltage, pulse period and number of electrical pulses during electroporation process with high viability and high efficiency of cell transfection.

Figure 2A:
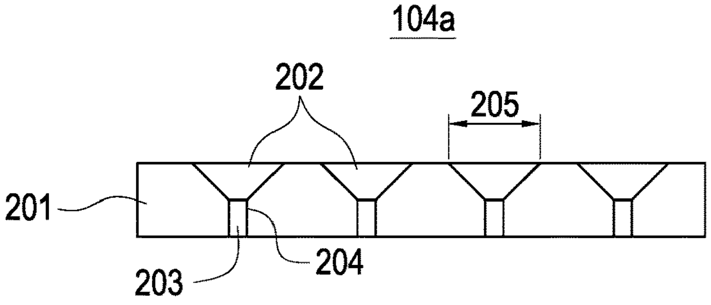
FIG. 2A shows the side view the MEMS filter for the exogenous molecules to pass through in the present disclosure.
Figure 2B:
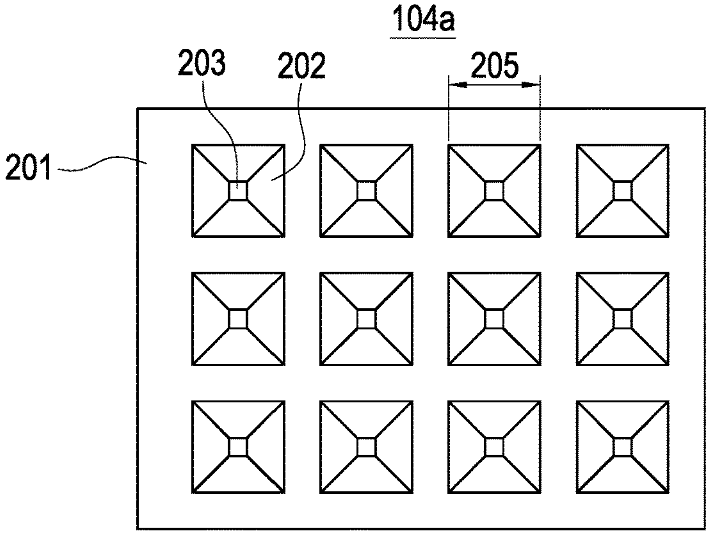
FIG. 2B shows the top view of the MEMS filter for the exogenous molecules to pass through in the present disclosure.

FIG. 2A shows the side view the MEMS filter 104*a* for the exogenous molecules to pass through in the present disclosure. FIG. 2B shows the top view of the MEMS filter 104*a* for the exogenous molecules to pass through in the present disclosure. As shown in FIG. 2A and FIG. 2B, one embodiment of the MEMS filter 104*a* is designed to allow the exogenous molecules to pass through the micro-holes of the funnel structure 202. The MEMS filter 104*a* is made of a silicon wafer through semiconductor process. The funnel structure 202 with multiple cavities are formed on the silicon wafer 201 by photolithography and wet etching process. The output holes (exit holes) 203 may be made by ICP (inductively coupled plasma) etching or dry etching. In some embodiments, the output hole 203 has the dimension of about 0.2 μm-1 μm, and the dimension of the opening 205 is about 20 μm-100 μm. The wall 204 of the funnel structure is structured to be a narrow neck only for the exogenous molecules to pass through. If the exogenous molecules fall into the opening 205 of the cavity by gravity after vibration, the V-shaped funnel structure 202 may lead the exogenous molecules to drop to the narrow neck of the funnel structure 202 and exit from the output hole 203 to the activation chamber 105 (shown in FIG. 1). The exogenous molecules are transfected into the cells through electroporation process. Since the output hole 203 of the MEMS filter 104*a* is mapped to be matched with the cell located in the cavity of the MEMS plate 104*b*, the transfection efficiency during electroporation process may be improved.

Figure 3A:
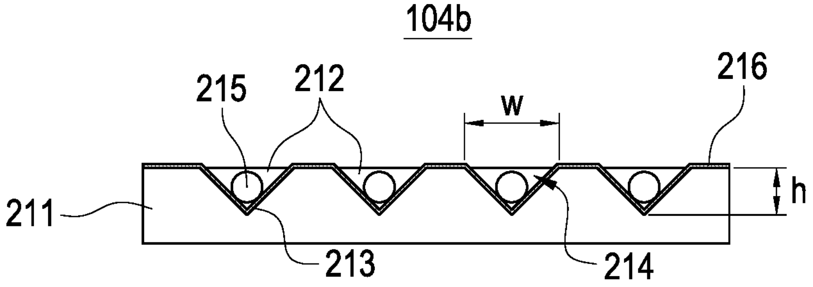
FIG. 3A shows the side view of the MEMS plate for fixing the cells in electroporation process of the present disclosure.
Figure 3B:
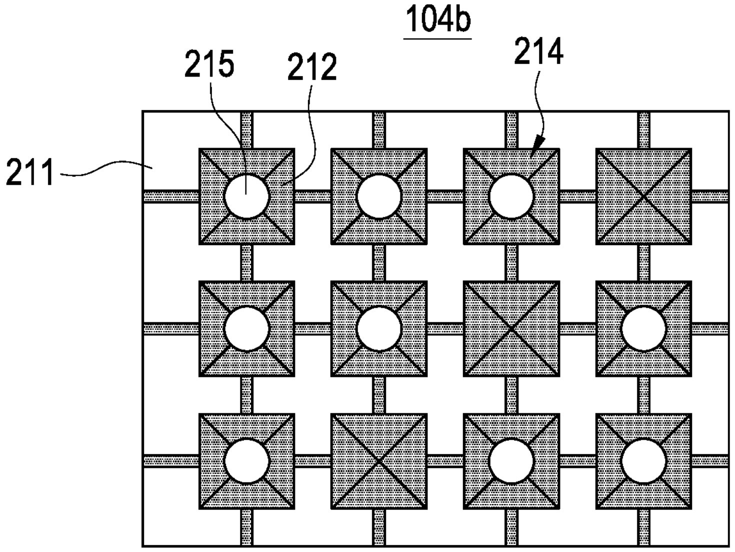
FIG. 3B shows the top view of the MEMS plate for fixing the cells in electroporation process of the present disclosure.

FIG. 3A shows the side view of the MEMS plate 104*b* for fixing the cells in electroporation process of the present disclosure. FIG. 3B shows the top view of the MEMS plate 104*b* for fixing the cells in electroporation process of the present disclosure. The V-shaped cavities 212 are formed on the silicon substrate 211 and made by wet etching of semiconductor process. A span angle defined between the cavity walls 213 is about 70.6° degrees on tip. The cell 215 may be located in the cavity 212 to be electroporated. The opening 214 of the cavity 212 has a dimension w and a depth h as illustrated in FIG. 3A. One embodiment of the metal layer (top metal layer) 216 of the MEMS plate 104*b* is disposed in the cavities 212 and connected between the cavities 212 in a mesh manner as illustrated in FIG. 3B. The metal layer 216 is capable of creating electric field toward the cell 215 located in the cavity 212.

FIG. 4A to FIG. 4H are the manufacturing process of the MEMS filter 104*a* of the present disclosure. The manufacture process of the MEMS filter 104*a* is made by micro machining of silicon wafer 201 as substrate through semiconductor process as shown in FIG. 4A to FIG. 4H. FIG. 4A to FIG. 4H illustrates the manufacturing process of one embodiment of the MEMS filter 104*a* with funnel structure that has better dimension control of diameter of the output hole 203. It should be noted that in FIG. 4A to FIG. 4H only one funnel structure is illustrated as an example, but the silicon wafer 201 may be formed with multiple funnel structures with the same process. In reality, multiple funnel structures within the same silicon wafer 201 may be fabricated simultaneously and cost effectively.

Figure 4A:
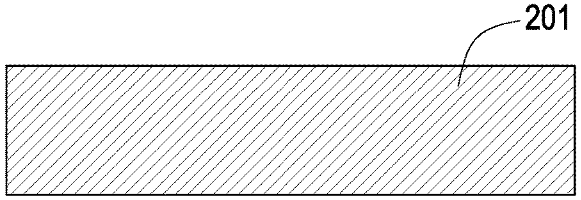
FIG. 4A to FIG. 4H are the manufacturing process of the MEMS filter of the present disclosure.
Figure 4B:
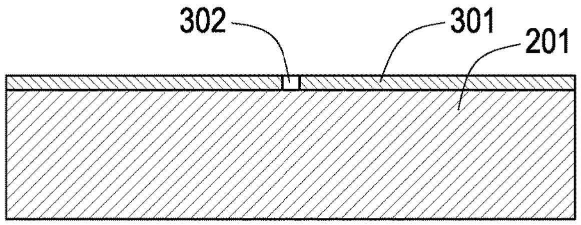
Figure 4C:
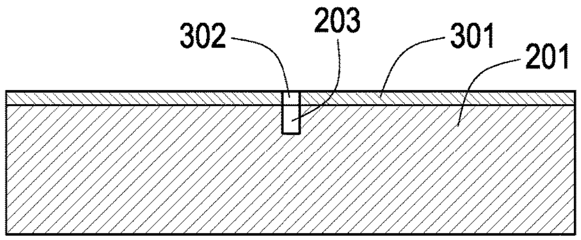
Figure 4D:
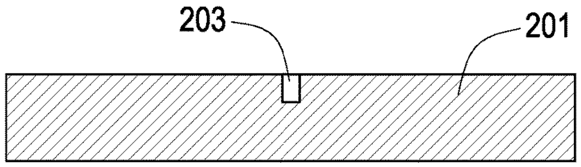
Figure 4E:
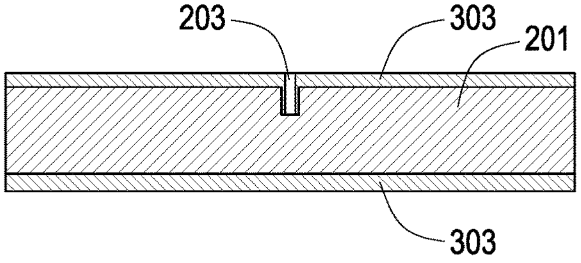
Figure 4F:
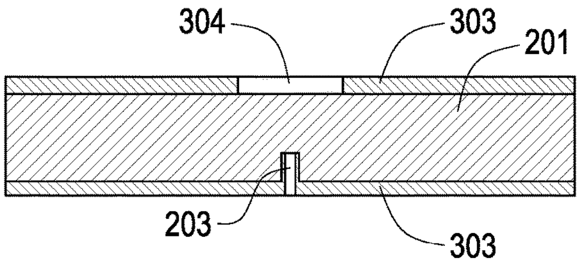
Figure 4G:
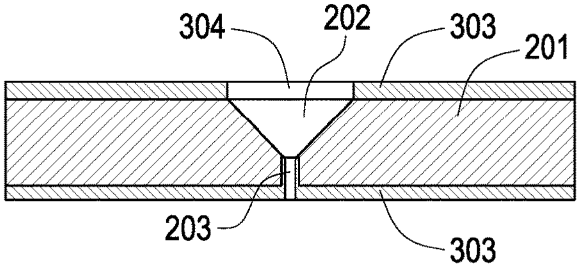
Figure 4H:
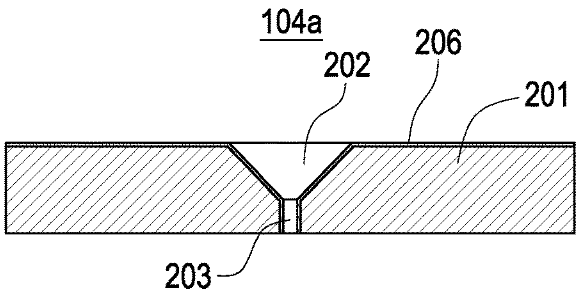

In FIG. 4A, the silicon wafer 201 provides as the silicon substrate. The silicon wafer 201 may be 6 inches to 12 inches in diameter. In FIG. 4B, by using photolithography, the metal mask layer 301 is formed on the silicon wafer 201 for defining the area 302 of the output hole. In FIG. 4C, the output hole (exit hole) 203 is formed after dry etching or ICP etching with the metal mask layer 301. In FIG. 4D, the metal mask layer (dry etching protection layer) 301 is removed, the silicon wafer 201 is thinned down in thickness by, for example, mechanical grinding plus polishing. In FIG. 4E, the protection layers 303 are re-grown on both sides of the silicon wafer 201. The material of the protection layer 303 may be, for example, silicon dioxide ($SiO_2$) or silicon nitride (SiN), or the combination of the two. It should be noted that the bottom wall of the output hole 203 has to be free from the protection layer 303. In other words, no protection layer 303 is disposed on the bottom wall of the output hole 203. In FIG. 4F, the silicon wafer 201 is flipped upside down, and then the cavity opening 304 is created by photolithography on the protection layer 303 opposite to the output hole 203. In FIG. 4G, the V-shaped cavity of the funnel structure 202 is created by the wet etching process with the protection layer 303. In FIG. 4H, the metal layer 206 is coated on the top surface of the MEMS filter 104*a*. As shown in FIG. 1, the metal layer 206 is connected to the negative terminal V− of the controller 107 during electroporation process. For the electroporation process, the controller 107 outputs voltage pulse with voltage level, pulse period and pulse number control. The applied voltage is positive to the MEMS plate 104*b* and negative to the MEMS filter 104*a*. The electroporation voltage is in the range of tens volts when the height of the activation chamber 105 is about 100 μm.

It is worth mentioning that, in order to make the output hole 203 in the cavity tip of the funnel structure 202, the silicon wafer 201 is desirably to be thinned down to about 100 μm to about 300 μm in thickness. The reason is that the cavity angle is about 70.6° after wet etching process. The larger diameter (shown in FIG. 2A and FIG. 2B) of the cavity opening 205, the thicker of the silicon wafer 201 may be used.

For example, the opening 205 with a diameter of 100 μm may be structured with a V-shaped cavity tip thickness of 70 μm. If the thickness of the silicon wafer 201 is more than 70 μm, the tip of the output hole 203 may not be made by single etching process. In FIG. 4B to FIG. 4D show the pattering in back side of the silicon wafer 201, and uses ICP etching or dry etching process to create a smaller vertical hole beneath the tip of V-shaped cavity. Generally, the ICP etching process may make a hole with the depth/hole ratio of 10:1 to 20:1. If the output hole 203 is set to be 1 μm in diameter, the ICP is used to create a hole with depth of 10 μm at least. Before wet etching process in FIG. 4G is started on top layer, the protection layer 303 needs to be coated on both sides of the silicon wafer 201 as shown in FIG. 4E and FIG. 4F.

As shown in FIG. 4A to FIG. 4H, the thickness of the silicon wafer 201 is mainly determined by the diameter of the cavity opening 205. The depth of the output hole 203 is determined by the hole diameter and the depth/hole ratio in the semiconductor process, which is generally limited to 20:1.

FIG. 5A to FIG. 5D are the manufacturing process of the MEMS plate 104*b* for fixing the cells of the present disclosure. It should be noted that in FIG. 5A to FIG. 5D only one cavity is illustrated as an example, but the silicon wafer 501 may be formed with multiple cavities with the same process. In reality, multiple cavities within the same silicon wafer 501 may be fabricated simultaneously and cost effectively.

Figure 5A:
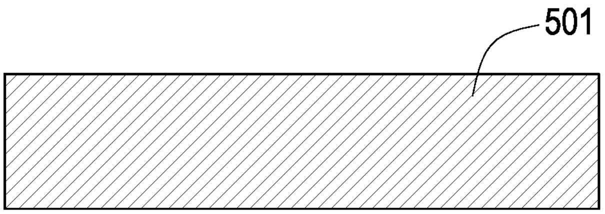
FIG. 5A to FIG. 5D are the manufacturing process of the MEMS plate for fixing the cells of the present disclosure.
Figure 5B:
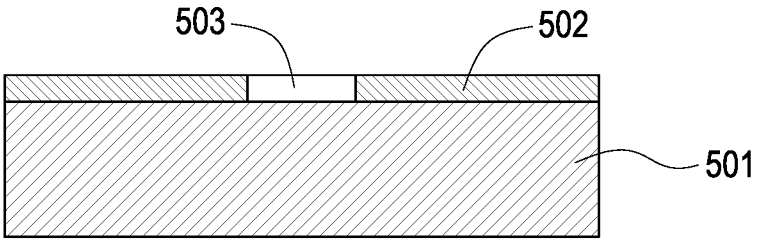
Figure 5C:
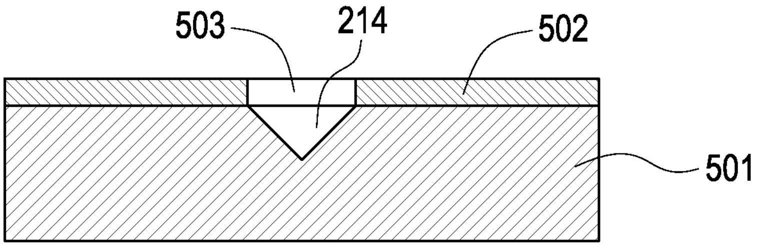
Figure 5D:
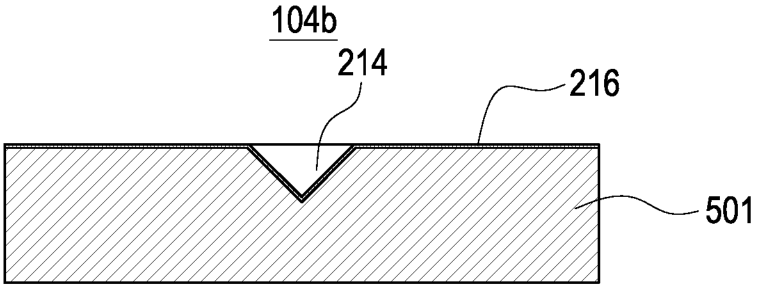

In FIG. 5A, the silicon wafer 501 to be used for the MEMS plate. In FIG. 5B, after the growth of the protection layer 502 (for example, $SiO_2$ and/or SiN) on top of silicon wafer 501, the pattern 503 of the cavity opening is formed on the protection layer 502 by photolithography. In FIG. 5C, the V-shapes opening 214 is formed with a tip. In FIG. 5D, the metal layer 216 is coated on the top surface of the MEMS plate (bottom MEMS plate) 104*b*. As shown in FIG. 1, the MEMS plate 104*b* is connected to the positive terminal V+ of the controller 107 during electroporation process, such that the cell membrane is kept at a positive potential to attract the negative charged exogenous molecule to pass through the membrane pore which is temporarily formed. The V-shaped cavity of the MEMS plate 104*b* is designed to be mapped with the output hole of the MEMS filter 104*a*, and allows the exogenous molecules to drop to the cells in the cavities of the MEMS plate 104*b*.

Figure 6:
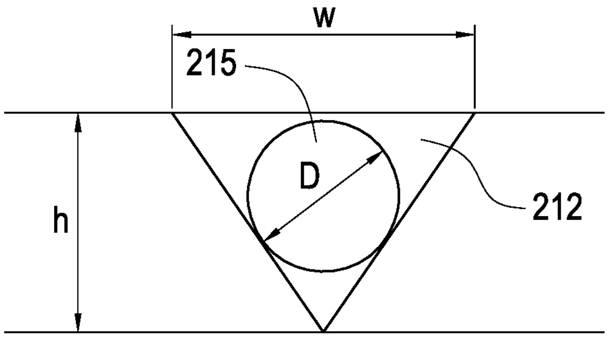
FIG. 6 is an enlarged view of the cavity inside the MEMS plate.

FIG. 6 is an enlarged view of the cavity inside the MEMS plate 104*b*. The cavity 212 has the opening dimension w and the depth h. The depth h is equal to w/1.41 (that is, h=w/1.41). If the cell 215 with diameter D needs to be fitted in the cavity 212, the minimum w is W=2.15D to make the cell 215 fixed beneath top surface of the MEMS plate 104*b*.

As shown in FIG. 1, after the electroporation process is finished, the solution may be fed to the first stage filter 102 to pass through the input valve 109*a* to the activation chamber 105. The ultrasound vibrator is operated intermittently together to push out the transfected cells through the output valve 109*b* to be outputted. The transfected cells are collected at the third phase.

In summary, comparing with the related art, the present disclosure discloses a microfluidic electroporation device for transfecting the exogenous molecules into the cells with high speed, high viability and high efficiency. The MEMS filter having the funnel structure is used, and the exogenous molecules being negative charged by the MEMS filter may pass through the narrow output hole. The output hole of the MEMS filter is one to one mapped to the cavity of the MEMS plate attached to the activation chamber. The cells to be transfected are fixed in the cavities of the MEMS plate with intermittent ultrasound vibration. The funnel structure of the MEMS filter for the exogenous molecules to pass through and the MEMS plate for fixing the cells to be transfected are both made by semiconductor process and wet etching. The microfluidic electroporation device of the disclosure is capable of transfecting multiple cells simultaneously with high viability and high efficiency.

The above is only a detailed description and drawings of the preferred embodiments of the present disclosure, but the features of the present disclosure are not limited thereto, and are not intended to limit the present disclosure. All the scope of the present disclosure shall be subjected to the scope of the following claims. The embodiments of the spirit of the present disclosure and its similar variations are intended to be included in the scope of the present disclosure. Any variation or modification that may be easily conceived by those skilled in the art and in the field of the present disclosure may be covered by the following claims.

What is claimed is:

1. A microfluidic electroporation device, comprising:

a first stage filter, configured to receive a mixture solution that comprises a plurality of cells and a plurality of impurities and filter the plurality of impurities from the plurality of cells;

an electroporation chamber assembly, comprising:

a first inlet valve;

an input chamber, connected with the first inlet valve, wherein the first inlet valve is configured to introduce a plurality of exogenous molecules into the input chamber;

a first outlet valve, connected with the input chamber;

a micro-electromechanical system (MEMS) filter, disposed beneath and attached to the input chamber, wherein the MEMS filter comprises a plurality of funnel structures arranged in a matrix form and a first top metal layer at least covering the plurality of funnel structures;

a second inlet valve, connected with the first stage filter;

an activation chamber, disposed beneath and attached to the MEMS filter and connected with the second inlet valve, wherein the plurality of cells enter the activation chamber from the first stage filter through the second inlet valve;

a second outlet valve, connected with the activation chamber; and a MEMS plate, disposed beneath and attached to the activation chamber and comprising a plurality of cavities arranged in a matrix form and a second top metal layer wherein each of the plurality of cavities are aligned with one of the plurality of funnel structures;

an ultrasound vibrator, disposed under the electroporation chamber assembly; and a controller, electrically connected with the ultrasound vibrator, configured to control the ultrasound vibrator to vibrate, and comprising a positive terminal connected with the MEMS plate and a negative terminal connected with the MEMS filter, wherein the controller is configured to actuate the ultrasound vibrator such that the plurality of cells in the activation chamber settle into the plurality of cavities of the MEMS plate, respectively;

wherein the plurality of exogenous molecules entering the input chamber through the first inlet valve are delivered by gravity through the plurality of funnel structures into the activation chamber, and excess exogenous molecules in the input chamber are exhausted through the first outlet valve;

wherein the controller is configured to apply a voltage across the positive terminal and the negative terminal to generate an electric field within the activation chamber such that the plurality of exogenous molecules in the activation chamber are accelerated toward the plurality of cells disposed within the plurality of cavities of the MEMS plate, thereby forming a plurality of transfected cells; and wherein the second outlet valve is configured to collect the plurality of transfected cells.

2. The microfluidic electroporation device of claim 1, wherein each funnel structure comprises an input hole facing the input chamber and an output hole facing the activation chamber, and the output hole is smaller than the input hole.

3. The microfluidic electroporation device of claim 2, wherein a diameter of the output hole is greater than or equal to 0.2 μm and less than or equal to 1 μm.

4. The microfluidic electroporation device of claim 1, wherein the MEMS filter is made of a silicon wafer.

5. The microfluidic electroporation device of claim 1, wherein the controller is configured to drive an amplitude, a duty cycle and/or a duration control of the ultrasound vibrator.

6. The microfluidic electroporation device of claim 1, wherein the controller is configured to control the first inlet valve, the first outlet valve, the second inlet valve, and the second outlet valve.

7. The microfluidic electroporation device of claim 1, wherein the controller is configured to control an electroporation process of the electroporation chamber assembly by a voltage control.

8. The microfluidic electroporation device of claim 7, wherein the controller is configured to control the electroporation process by controlling an electroporation voltage, a pulse interval and/or a pulse number.

9. The microfluidic electroporation device of claim 1, wherein the ultrasound vibrator is made of a piezoelectric material.

10. The microfluidic electroporation device of claim 9, wherein the piezoelectric material is PZT.

11. The microfluidic electroporation device of claim 9, wherein the ultrasound vibrator is configured to operate intermittently with a frequency range of greater than or equal to 20 Khz and less than or equal to 200 Khz.

12. The microfluidic electroporation device of claim 1, wherein the MEMS filter comprises a V-shaped cavity made by a wet etching process.

13. The microfluidic electroporation device of claim 1, wherein the MEMS plate comprises a V-shaped cavity made by a wet etching process.

* * * * *